(12) United States Patent
Cohan et al.

(10) Patent No.: US 6,196,993 B1
(45) Date of Patent: Mar. 6, 2001

(54) OPHTHALMIC INSERT AND METHOD FOR SUSTAINED RELEASE OF MEDICATION TO THE EYE

(75) Inventors: Bruce E. Cohan; Howard Diamond, both of Ann Arbor, MI (US)

(73) Assignee: Eyelab Group, LLC, Ann Arbor, MI (US)

( * ) Notice: Subject to any disclaimer, the term of this patent is extended or adjusted under 35 U.S.C. 154(b) by 0 days.

(21) Appl. No.: 09/294,720

(22) Filed: Apr. 19, 1999

Related U.S. Application Data

(60) Provisional application No. 60/082,360, filed on Apr. 20, 1998.

(51) Int. Cl.[7] .................................................. A61K 9/22
(52) U.S. Cl. ...................................... 604/89.1; 604/93.01
(58) Field of Search ............................... 604/89.1, 891.1, 604/294, 22, 93, 257, 285, 289, 300; 222/187

(56) References Cited

U.S. PATENT DOCUMENTS

| | | |
|---|---|---|
| 3,618,604 | 11/1971 | Ness . |
| 3,625,214 | 12/1971 | Higuchi . |
| 3,626,940 | 12/1971 | Zaffaroni . |
| 3,630,200 | 12/1971 | Higuchi . |
| 3,641,237 | 2/1972 | Gould et al. . |
| 3,826,258 | 7/1974 | Abraham . |
| 3,845,770 | 11/1974 | Theeuwes et al. . |
| 3,949,750 | * 4/1976 | Freeman ............................... 128/260 |
| 3,962,414 | 6/1976 | Michaels . |
| 3,963,025 | 6/1976 | Whitaker et al. . |
| 3,992,071 | 11/1976 | Higuchi et al. . |
| 4,014,335 | 3/1977 | Arnold . |
| 4,834,979 | * 5/1989 | Gale ....................................... 424/448 |
| 4,875,602 | * 10/1989 | Chickering et al. ................. 222/187 |
| 4,882,150 | 11/1989 | Kaufman . |
| 4,923,699 | 5/1990 | Kaufman . |
| 4,994,273 | 2/1991 | Zentner et al. . |
| 5,053,030 | 10/1991 | Herrick et al. . |
| 5,171,270 | 12/1992 | Herrick et al. . |
| 5,283,063 | 2/1994 | Freeman . |
| 5,378,475 | 1/1995 | Smith et al. . |
| 5,417,651 | 5/1995 | Guena et al. . |
| 5,417,682 | 5/1995 | Wong et al. . |
| 5,423,777 | * 6/1995 | Tajiri et al. ........................... 604/294 |
| 5,723,005 | 3/1998 | Herrick . |
| 5,725,493 | * 3/1998 | Avery et al. .............................. 604/9 |

OTHER PUBLICATIONS

Oasis Advertisement, Ophthalmology Management, Mar. 1998, p. 33.
FCI Advertisment, Ophthalmology Management, Mar. 1998, p. 7.
EagleVision Advertisment.

* cited by examiner

*Primary Examiner*—Sharon Kennedy
*Assistant Examiner*—Catherine Serke
(74) *Attorney, Agent, or Firm*—Brooks & Kushman P.C.

(57) ABSTRACT

An ophthalmic insert and method for sustained release of medication to the eye are provided. The insert includes a body portion sized to pass through a lacrimal punctum and be positioned within a lacrimal canaliculus of the eyelid. The insert further includes a collarette connected to the body portion and sized to rest on the exterior of the lacrimal punctum, the collarette having a pore provided therein. A reservoir is contained at least partially within the body portion and in fluid communication with the pore, wherein the reservoir is designed to store and release medication through the pore and onto the eye over time in a controlled manner while the insert is positioned in the eyelid. Preferably, the pore is constructed with a specific geometry appropriate to control the rate of release of the medication onto the eye.

20 Claims, 3 Drawing Sheets

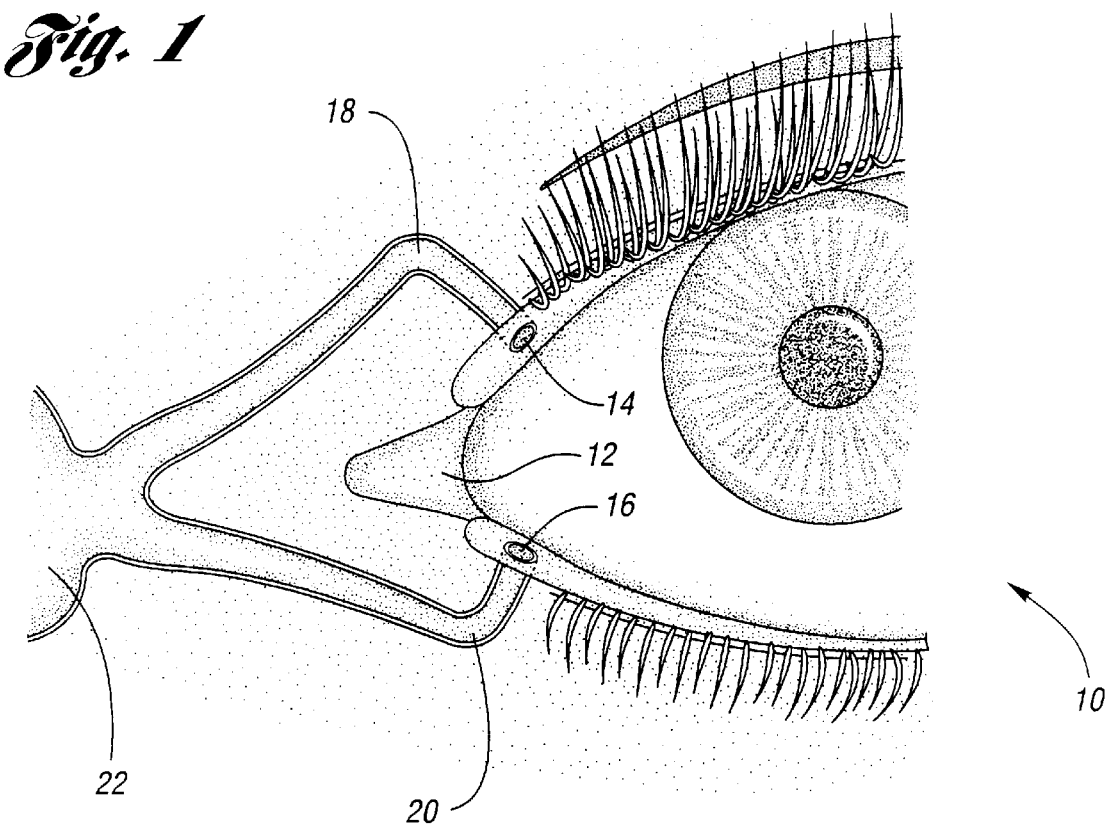
Fig. 1
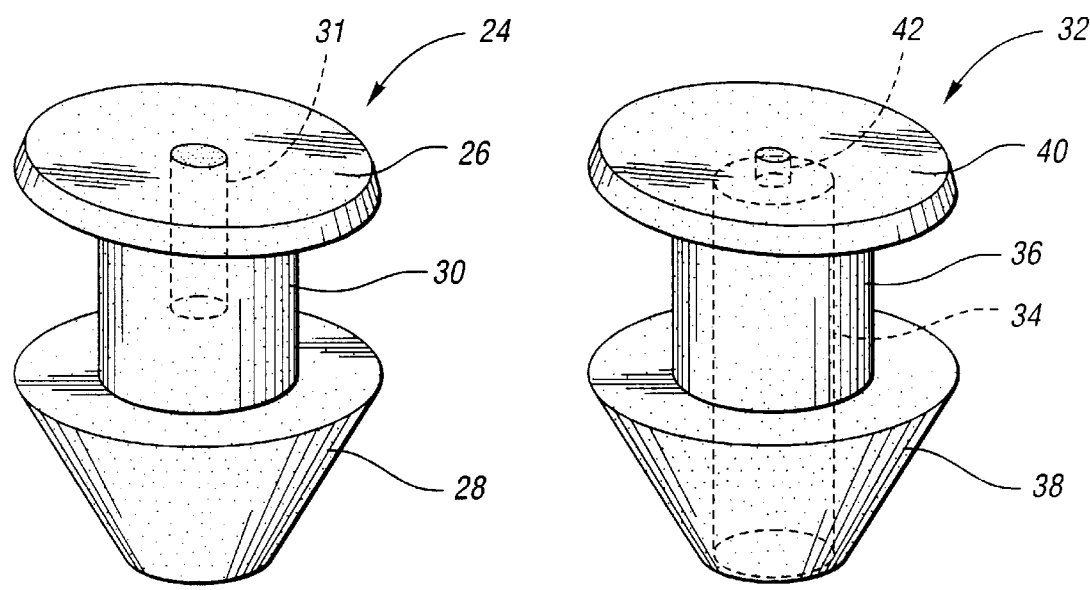
Fig. 2
*(PRIOR ART)*
Fig. 3

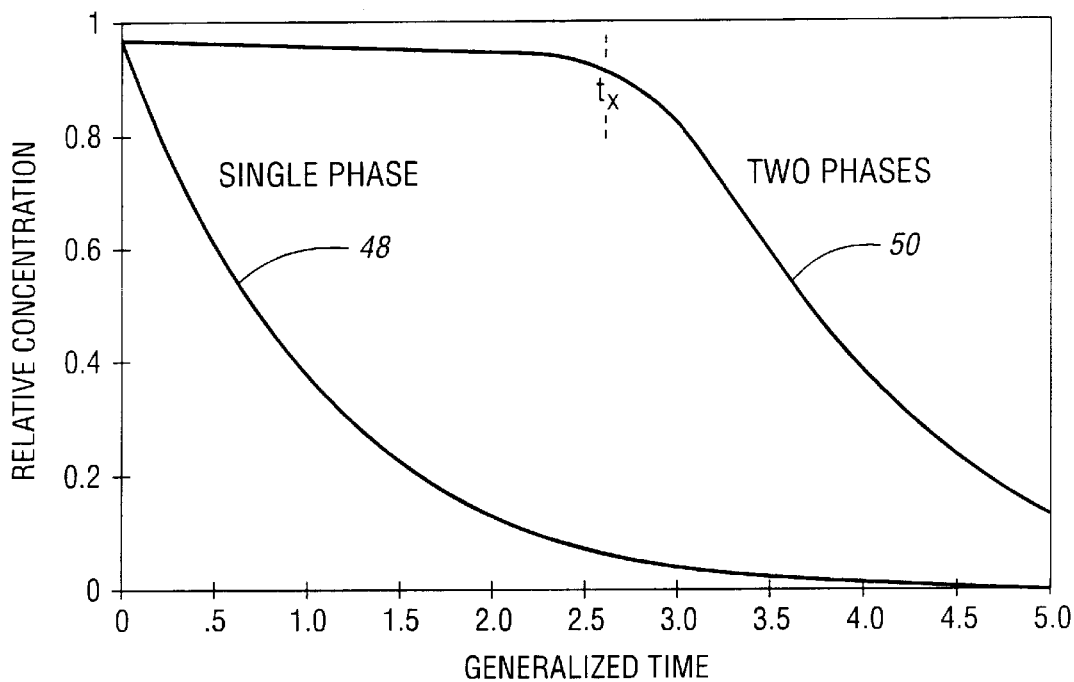
Fig. 8
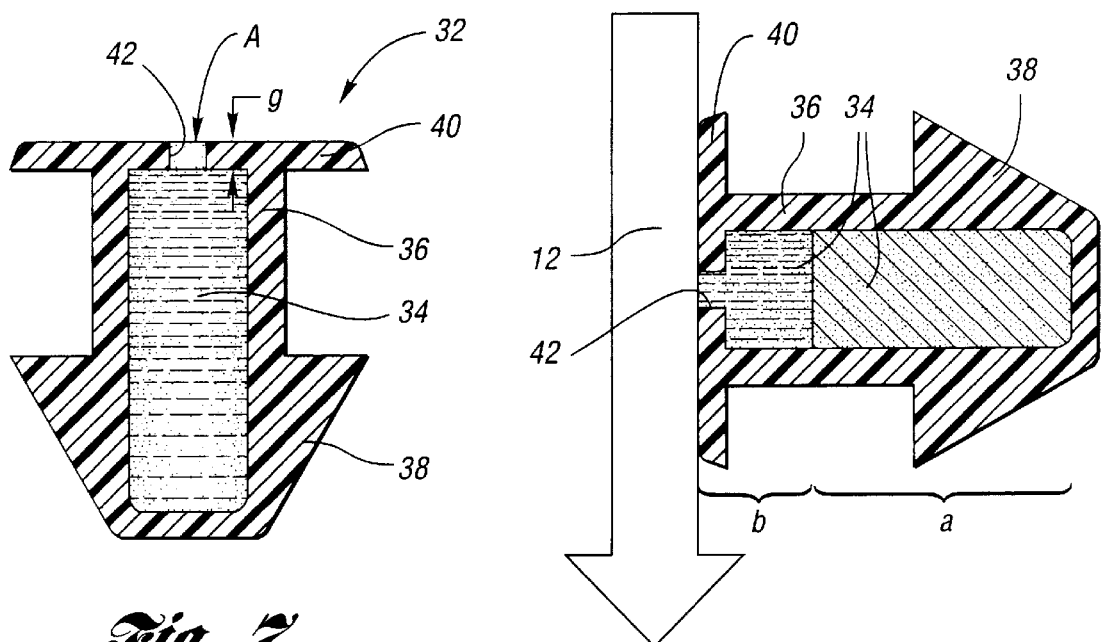
Fig. 7
Fig. 9

OPHTHALMIC INSERT AND METHOD FOR SUSTAINED RELEASE OF MEDICATION TO THE EYE

CROSS-REFERENCE TO RELATED APPLICATIONS

This application claims the benefit of U.S. provisional application Ser. No. 60/082,360 filed Apr. 20, 1998.

TECHNICAL FIELD

This invention relates to an ophthalmic insert and method for the sustained release of medication to the eye for the treatment of eye disorders.

BACKGROUND ART

In order to treat infection, inflammation, glaucoma, and other ocular diseases, drugs are often required to be administered to the eye. A conventional method of drug delivery is by topical application to the eye's surface. The eye is uniquely suited to this surface route of drug administration because, properly constituted, drugs can penetrate through the cornea, rise to therapeutic concentration levels inside the eye, and exert their beneficial effects. In practice, eye drops currently account for more than 95% of drug delivery methods for the eye. Rarely are drugs for the eye administered orally or by injection, either because they reach the eye in too low a concentration to have the desired pharmacological effect, or because their use is complicated by significant systemic side effects.

Eye drops, though effective, are unrefined and inefficient. When an eye drop is instilled in the eye, it overfills the conjunctival sac, the pocket between the eye and the lids, causing a substantial portion of the drop to be lost due to overflow of the lid margin onto the cheek. In addition, a substantial portion of the drop remaining on the ocular surface is washed away by tears into the tear drainage system, thereby diluting the concentration of the drug. Not only is this share of the drug dose lost before it can cross the cornea, but this excess drug may be carried into the nose and throat where it is absorbed into the general circulation, sometimes leading to serious systemic side effects. The small portion of the drug in the eye drop which does penetrate the cornea results in an initial peak tissue concentration, a higher level than is required for the initial pharmacological effect. The tissue concentration then gradually decreases, such that by the time the next eye drop is due, the tissue concentration and the intended pharmacological effect may be too low.

To compound the problems described above, patients often do not use their eye drops as prescribed. Often, this poor compliance is due to an initial stinging or burning sensation caused by the eye drop. Certainly, instilling eye drops in one's own eye can be difficult, in part because of the normal reflex to protect the eye. Therefore, sometimes one or more drops miss the eye. Older patients may have additional problems instilling drops due to arthritis, unsteadiness, and decreased vision, and pediatric and psychiatric patient populations pose difficulties as well.

Attempts have been made to relieve these limitations of topical medications through systems that provide sustained drug release to the eye. Prior topical sustained release systems include gradual release formulations, either in solution or ointment form, which are applied to the eye in the same manner as eye drops but less frequently. Such formulations are disclosed, for example, in U.S. Pat. No. 3,826,258 issued to Abraham and U.S. Pat. No. 4,923,699 issued to Kaufman. Due to their method of application, however, these formulations result in many of the same problems detailed above for conventional eye drops. In the case of ointment preparations, additional problems are encountered such as a blurring effect on vision and the discomfort of the sticky sensation caused by the thick ointment base.

Alternatively, sustained release systems have been configured to be placed into the conjunctival cul-de-sac, between the lower lid and the eye. Such units typically contain a core drug-containing reservoir surrounded by a hydrophobic copolymer membrane which controls the diffusion of the drug. Examples of such devices are disclosed in U.S. Pat. No. 3,618,604 issued to Ness, U.S. Pat. No. 3,626,940 issued to Zaffaroni, U.S. Pat. No. 3,845,770 issued to Theeuwes et al., U.S. Pat. No. 3,962,414 issued to Michaels, U.S. Pat. No. 3,993,071 issued to Higuchi et al., and U.S. Pat. No. 4,014,335 issued to Arnold. However, due to their positioning, the units are uncomfortable and poor patient acceptance is again encountered.

DISCLOSURE OF INVENTION

Therefore, it is an object of the present invention to provide an ophthalmic device and method which provide sustained release of medication to the eye.

It is a further object of the present invention to provide an ophthalmic device and method that ensure controlled medication delivery to the eye over an extended period of time.

It is a still further object of the present invention to provide an ophthalmic device and method for sustained release of medication to the eye which improve patient compliance.

Accordingly, an ophthalmic insert for sustained release of medication to the eye is provided. The insert includes a body portion sized to pass through a lacrimal punctum and be positioned within a lacrimal canaliculus of an eyelid. The insert further includes a collarette connected to the body portion and sized to rest on the exterior of the lacrimal punctum, the collarette having a pore provided therein. A reservoir is contained at least partially within the body portion and in fluid communication with the pore, wherein the reservoir is designed to store and release medication through the pore and onto the eye over time in a controlled manner while the insert is positioned in the eyelid.

Correspondingly, a method is for providing sustained release of medication to the eye is provided. The method includes providing an insert having a body portion sized to pass through a lacrimal punctum and be positioned within a lacrimal canaliculus of an eyelid, a collarette connected to the body portion and sized to rest on the exterior of the lacrimal punctum and having a pore provided therein, and a reservoir contained at least partially within the body portion and in fluid communication with the pore. The method further includes positioning the insert into the lacrimal punctum and canaliculus of the eyelid. Still further, the method includes releasing medication stored in the reservoir through the pore and onto the eye over time in a controlled manner while the insert is positioned in the eyelid.

In a preferred embodiment, the insert is positioned in the upper lacrimal punctum and canaliculus, so as to minimize disruption of the normal flow of tears. In addition, the pore is preferably constructed with a specific geometry appropriate to control the rate of release of the medication onto the eye. The insert may further comprise an enlarged bulb portion connected to the body portion for securing the insert within the canaliculus. The reservoir may be partially contained within the bulb portion, and may also be in fluid communication with a reservoir extension, such as a balloon, which extends into the canaliculus to allow for additional medication volume.

The above objects and other objects, features, and advantages of the present invention are more readily understood from a review of the attached drawings and the accompanying specification and claims.

BRIEF DESCRIPTION OF DRAWINGS

FIG. 1 shows the anatomy of the lacrimal drainage system of the human eye;

FIG. 2 shows an example of a conventional punctal occluder;

FIG. 3 is a perspective view of the ophthalmic insert of the present invention;

FIG. 7 is a sectional view showing medication within the reservoir of the ophthalmic insert;

FIG. 8 is a graph of the diffusion of medication from the reservoir into the eye for different drug configurations within the reservoir; and FIG. 9 is a schematic representation of a preferred configuration of medication within the reservoir and its contact with the external tear flow.

BEST MODE FOR CARRYING OUT THE INVENTION

Figure 4:
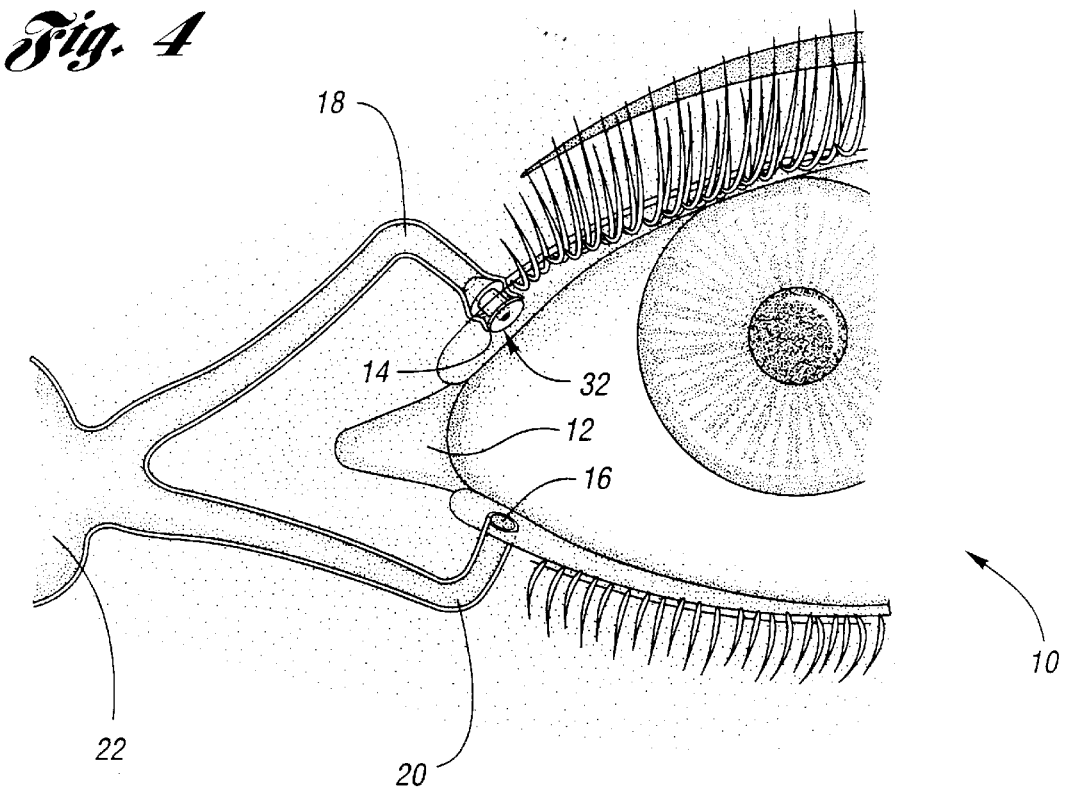
FIG. 4 is an illustration of the ophthalmic insert as it is positioned in the hum an lacrimal drainage system.

As a matter of background, FIG. 1 shows the anatomy of the drainage system of the eye 10. Tears are produced by the lacrimal gland (not shown) superior to the outer portion of each eye 10. Tears flow across the surface of the eye 10 to a shallow pool, termed the lacrimal lake 12, located where the eyelids come together at their inner ends. From there, the tears drain through small openings in each of the eyelids, namely the upper lacrimal punctum 14 and the lower lacrimal punctum 16. From the upper 14 and lower 16 puncta, the tears pass into the upper lacrimal canaliculus 18 and lower lacrimal canaliculus 20, respectively, which are duct-like pathways leading to the lacrimal sac 22. The lacrimal sac 22 is the superior, expanded portion of the nasolacrimal duct (not shown) which drains tears into the nasal system. The upper lacrimal punctum 14 and canaliculus 18 are said to drain only about 10% of the tears from the eye 10, such that their obstruction virtually never leads to tear overflow.

Insufficient tears, or "dry eye", is a common condition caused by insufficient production of tears from the lacrimal gland which causes symptoms such as dryness, redness, burning, reflex tearing, itching, or foreign body sensation. In especially difficult cases of dry eye, a punctal occluder may be placed into one or both of the lacrimal puncta 14, 16. Punctal occluders prevent the tears, which are being produced in deficient volume by the lacrimal gland, from draining into the lacrimal canaliculi 18, 20. Punctal occluders can be secured in the lacrimal puncta 14, 16 without anesthesia and removed with ease when necessary.

As shown in FIG. 2, a punctal occluder 24 typically includes a collarette 26 which rests on the exterior of the punctum 14, 16, a bulb 28 that blockingly projects into the canaliculus 18, 20, and a body portion 30 connecting the collarette 26 and the bulb 28. Commercially available punctal occluders usually have a length of approximately 2.0 mm, and differ from each other only slightly in configuration. All of their bulbs 28 are designed to prevent the occluder 24 from being easily dislodged from the canaliculus 18, 20, and may be tapered for ease of insertion into the puncta 14, 16. Their collarettes 26 are designed to have a diameter to prevent the occluder 24 from completely entering the canaliculus 18, 20, and are preferably smooth to minimize irritation of the eye 10. The body portions 30 of different punctal occluders 24 are similar and essentially a non-functional connection between the collarette 26 and the bulb 28 portions. The collarette 26 may include an aperture 31 extending into the body portion 30 to aid in grasping the occluder 24 during its insertion into the puncta 14, 16. Examples of punctal occluders can be found in U.S. Pat. Nos. 3,949,750 and 5,283,063 issued to Freeman, U.S. Pat. Nos. 5,053,030; 5,171,270; and 5,723,005 issued to Herrick, U.S. Pat. No. 5,417,651 issued to Guena et al., and U.S. Pat. No. 5,423,777 issued to Tajiri et al.

Against this background, the ophthalmic insert device of the present invention, designated generally by reference numeral 32, is illustrated in FIG. 3. In a preferred embodiment, ophthalmic insert 32 adapts the form of a conventional punctal occluder 24 to incorporate a reservoir 34 designed to store and release medication onto the surface of the eye 10 in a continuous, long-term manner. Ophthalmic insert 32 can be molded or otherwise formed from a flexible material, such as silicone, that is impermeable to the medication which will fill the reservoir 34. Reservoir 34 is formed by a channel through the interior of a body portion 36 of insert 32. Preferably, body portion 36 is flexible, and may even be accordion-shaped to provide the capability of lengthwise expansion as it is filled with medication.

Still referring to FIG. 3, a collarette 40 anchors the insert 32 to the exterior of the lacrimal punctum 14, 16, and is provided with a pore 42 in fluid communication with reservoir 34. In order to control the delivery of a specific medication, the geometry of pore 42 may be customized as will be explained below. Through pore 42, medication is deployed from reservoir 34 into the tears of the lacrimal lake 12 where the medication mixes, as eye drops do, with the tears and penetrates the eye 10 to have the intended pharmacological effect. Although not required, an enlarged bulb portion 38 may be provided to help secure the insert 32 within the canaliculus 18 and also to provide additional volume for reservoir 34 as shown.

FIG. 4 shows ophthalmic insert 34 of the present invention filled with medication and positioned in the upper lacrimal drainage system. In contrast to prior art sustained release devices, ophthalmic insert 32 of the present invention improves patient compliance through its comfortable placement in a relatively non-essential eye orifice. Positioning the insert 32 in the upper lacrimal punctum 14 and canaliculus 18, as shown, is preferred due to their low percentage of tear drainage as compared with the lower lacrimal drainage system. With this positioning, ophthalmic insert 32 can perform its sustained release function without affecting the normal flow of tears.

As with conventional punctal occluders, insert 32 may be positioned and removed non-surgically and without anesthesia. In practice, the canaliculus 18 is prepared for positioning of the insert 32 through dilation with a tapered rod. The canaliculus 18 is surrounded by elastic tissue that permits it to be dilated to allow for entry of the insert 32, and subsequently resume a tight hold on the insert 32 to prevent its accidental removal. After dilation, an inserting tool similar to forceps may be used to position the insert 32 into the punctum 14. Ophthalmic insert 32 can be placed in the punctum 14 pre-filled with medication, or alternatively may be filled after placement from a syringe-type device. The latter method is advantageous in that the insert 32 could be refilled with medication without requiring its removal. When it is desired to remove the insert 32 from the punctum 14, the collarette 40 is easily grasped with forceps, force applied, and the insert withdrawn.

Figure 5:
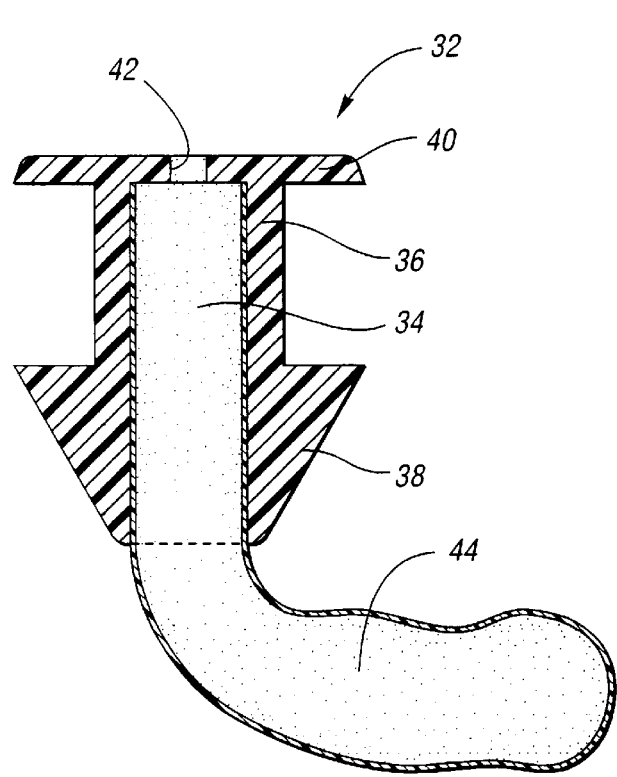
FIG. 5 is a sectional view of the ophthalmic insert utilizing a reservoir extension.

In order to increase the volume of the reservoir 34 beyond that available in the body portion 36 and bulb 38 of the ophthalmic insert 32, a reservoir extension 44 may be provided in fluid communication with reservoir 34 as shown in FIG. 5. In a preferred embodiment, reservoir extension 44 comprises an expansile, balloon-like component that extends into the canaliculus 18. Reservoir extension 44 can be molded as an integral part of the insert 32, or alternatively can be attached to body portion 36 or bulb 38 as an additional part.

Figure 6:
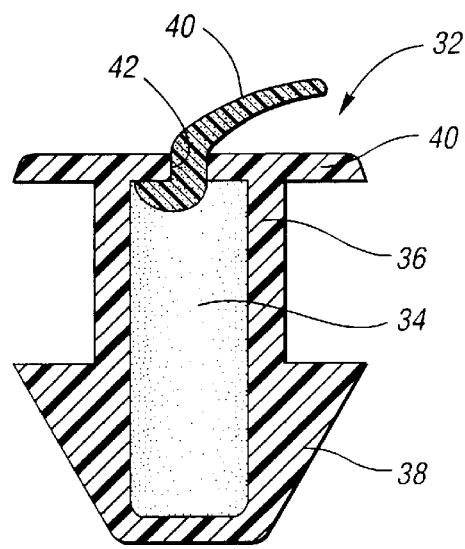
FIG. 6 is a sectional view of the ophthalmic insert utilizing a wick extension from the reservoir.

In the embodiment of ophthalmic insert 32 shown in FIG. 6, a wick extension 46 from the reservoir 34 is provided to aid in medication release onto the surface of the eye 10. Wick extension 46 is preferably secured within the reservoir 34 in fluid communication with the medication stored therein, and extends through pore 42 in collarette 40 to rest in the lacrimal lake 12. Wick extension 46 should be formed of a material suitable to transmit medication from reservoir 34 to the lacrimal lake 12, preferably an absorbent, cloth-like material which can rest in the lacrimal lake 12 without causing irritation. The use of wick extension 46 assures constant contact of insert 32 with the tear stream, and also provides an additional aid for removal of the insert 32.

FIG. 7 shows the ophthalmic insert 32 of the present invention with its reservoir 34 filled with medication. The transfer of medication from the reservoir 34 onto the surface of the eye 10 takes place by diffusion. A gradient region (g) is defined by the length from the reservoir 34 to the outlet of pore 42. Medication flows along gradient (g), through pore 42 having cross-sectional area (A), and into the tears in lacrimal lake 12 which replace the medication by the diffusion process. Depending on the required tear medication concentration, the medication can be in the form of a solid, a concentrated aqueous or other solution, a resin suspension, encapsulated within biodegradable microspheres such as liposomes or other suitable nano-composites, or in a combination of these different configurations.

Diffusion of the medication out of reservoir 34 is controlled by the following equations, Fick's Laws of Diffusion:

$$\frac{\partial c}{\partial t} = D \frac{\partial^2 c}{\partial x^2} \quad (1)$$

$$J = -D \frac{\partial c}{\partial x} \quad (2)$$

where c represents concentration, D represents the diffusion coefficient, J is the flux density (flow per unit cross-sectional area), x is the distance along the direction of flow, and t is time. For the ophthalmic insert 32 of the present invention, equation 2 becomes:

$$J = D \frac{c_i - c_o}{g} \quad (3)$$

where $c_i$ is the medication concentration within the reservoir 34 adjacent to its pore 44, and $c_o$ is the medication concentration in the tears just outside the reservoir 34. The value of $c_o$ is very near zero if tear flow in the lacrimal lake 12 sweeps the medication away from the pore 44.

FIG. 8 is a graph of the diffusion of medication from reservoir 34 into the lacrimal lake 12 for different medication configurations. The diffusion of a single phase, or concentration, of medication within the reservoir 34 is indicated by reference numeral 48. As shown, as soon as the diffusion process begins, the concentration, $c_i$, and the flux, J, change with time so that the medication delivery rate decreases exponentially by first order chemical kinetics. Advantageously, a range of reservoir drug configurations can be used to fit the needs of different patients or the changing requirements over time of an individual patient.

In a preferred embodiment shown schematically in FIG. 9, the reservoir 34 includes a region (a) containing the most concentrated form of the medication, in either a solid or liquid state. The medication diffuses from region (a) into an adjacent region (b), nearest the pore 42, containing a saturated solution of the medication. Preferably, the concentrated form of the medication in region (a) should be sparingly soluble in saline or water in order to assure a constantly saturated region (b). Referring again to FIG. 8, the diffusion of this two phase configuration is indicated by reference numeral 50. The two-phase configuration will cause the rate of medication release to be constant, since the concentrated medication in region (a) maintains a constant saturated concentration, $c_i$, in region (b). The saturated solution (b) will remain saturated as medication is released as long as the concentrated form in region (a) is present. In the example shown in FIG. 8, the concentrated medication is exhausted at the time $t_x$.

The geometry of the pore 42 leading from the reservoir 34 to the lacrimal lake 12 controls the rate of flow, I, of medication from the ophthalmic insert 32 by:

$$I = JA = \frac{Dc_i A}{g} \quad (4)$$

Therefore, for a given diffusion coefficient, D, and a given concentration of the medication in the saturated phase, $c_i$, I is controlled by the geometry of the pore 42 (A/g). Using this information, the appropriate geometry of pore 42 necessary to achieve a desired medication flow rate over time can be calculated. The rate-controlling pore 42 can be formed with specific dimensions at the time the insert 32 is made, or pore 42 could be sized appropriately by retrofitting insert 32 with an apertured cap of appropriate geometry fit over reservoir 34. In an alternative embodiment, pore 42 could be provided in the form of an imperforate material placed over the collarette 40 that is permeable to the passage of the medication.

Although medication release from the reservoir 34 is controlled primarily by diffusion, secondary factors such as gravity, inertia from the rapid downward component of each eyelid blink, and muscular forces within the lid may favor release of the medication from reservoir 34. In addition, a micropump could be employed within the ophthalmic insert 32 to forcibly expel medication from reservoir 34 at a chosen rate.

Replacing eye drops with the ophthalmic insert 32 of the present invention will enhance convenience for patients who presently require the long-term use of eye medication. In addition, the insert of the present invention will eliminate the major problem in their medical management, inconsistent patient compliance. Importantly, insert 32 of the present invention offers the patient the benefit of a continuous pharmacologic effect, as opposed to the initial peak medication concentration and gradual decrease in therapeutic action encountered with eye drops. Therefore, the quality of medical care will be improved in those eye diseases requiring extended use of eye medications.

The four currently most important anti-glaucoma drugs, each of which is supplied only as eye drops in aqueous solution, are immediate candidates for administration via the insert 32 of the present invention. The four drugs, namely timolol, dorzolamide hydrochloride, latanoprost, and brimonidine, are potent drugs with long durations of action, evidenced by their relatively low concentration in eye drops and their low frequency of administration (see: 1998 Physicians' Desk Reference for Ophthalmology).

When released using the insert 32 of the present invention, some agents may now be able to achieve effective concentrations in target tissues that are currently partially or completely inaccessible to conventional topical application. Possible agents to be released by insert 32 include those for antimicrobial therapy, including antiviral agents for herpes simplex, zoster keratitis, and possibly cytomegalovirus retinitis, antifungal and antibiotic agents for keratitis and possibly endophthalmitis, nonsteroidal and steroid anti-inflammatory medications for the many inflammatory diseases and inflammatory components of eye disorders, and new agents like those with neuroprotective properties for ganglion cells and/or optic nerve axons in glaucoma, as well as gene delivery to ocular tissues. Further, the insert and method of the present invention may make it possible to treat the eye with medications not now suitable for eye drop formulation, such as drugs which are chemically unstable in tears and so have too short a duration of action, or have other limiting characteristics.

While embodiments of the invention have been illustrated and described, it is not intended that these embodiments illustrate and describe all possible forms of the invention. Rather, the words used are words of description rather than limitation, and it is understood that various changes may be made without departing from the spirit and scope of the invention.

What is claimed is:

1. An ophthalmic insert for sustained release of medication to an eye, comprising:
    a body portion sized to pass through a lacrimal punctum and be positioned within a lacrimal canaliculus of an eyelid;
    a collarette connected to the body portion and sized to rest on the exterior of the lacrimal punctum, the collarette having at least one pore provided therein;
    a reservoir contained at least partially within the body portion and in fluid communication with the at least one pore; and
    a medication stored within the reservoir and released through the at least one pore and onto the eye over time in a controlled manner while the insert is positioned in the eyelid.

2. The ophthalmic insert of claim 1, further comprising an enlarged bulb portion connected to the body portion for securing the insert within the canaliculus.

3. The ophthalmic insert of claim 2, wherein the reservoir is at least partially contained within the bulb portion.

4. The ophthalmic insert of claim 1, further comprising a reservoir extension in fluid communication with the reservoir and adapted to extend into the canaliculus.

5. The ophthalmic insert of claim 4, wherein the reservoir extension comprises a balloon.

6. The ophthalmic insert of claim 1, wherein the at least one pore is formed in the collarette.

7. The ophthalmic insert of claim 1, wherein the at least one pore comprises an apertured cap fit over the reservoir.

8. The ophthalmic insert of claim 1, wherein the at least one pore comprises an imperforate membrane that is selectively permeable to the medication and covers the collarette.

9. The ophthalmic insert of claim 1, wherein the body portion is flexible.

10. The ophthalmic insert of claim 1, further comprising a wick extension secured within the reservoir and in fluid communication with the medication stored therein, the wick extension extending through the at least one pore to facilitate releasing the medication onto the eye.

11. The ophthalmic insert of claim 1, wherein the insert adapted to be positioned in the upper lacrimal punctum and canaliculus.

12. The ophthalmic insert of claim 1, wherein the medication is stored in the reservoir in a configuration having two phases, the two phases comprising a concentrated form and a saturated solution.

13. The ophthalmic insert of claim 1, wherein the insert is formed of a material impermeable to the medication.

14. The ophthalmic insert of claim 1, wherein the at least one pore is constructed with a specific geometry appropriate to control the rate of release of the medication onto the eye.

15. A method for providing sustained release of medication to an eye, the method comprising:
    providing an ophthalmic insert having a body portion sized to pass through a lacrimal punctum and be positioned within a lacrimal canaliculus of an eyelid, a collarette connected to the body portion and sized to rest on the exterior of the lacrimal punctum and having at least one pore provided therein, a reservoir contained at least partially within the body portion and in fluid communication with the at least one pore, and a medication stored within the reservoir;
    positioning the insert into the lacrimal punctum and canaliculus of the eyelid; and
    releasing the medication stored in the reservoir through the at least one pore and onto the eye over time in a controlled manner.

16. The method of claim 15, wherein positioning the insert comprises positioning the insert into an upper lacrimal punctum and canaliculus.

17. The method of claim 15, wherein positioning the insert includes positioning the insert pre-filled with the medication.

18. The method of claim 15, further comprising filling the insert with the medication following positioning the insert in the lacrimal punctum and canaliculus.

19. The method of claim 15, wherein releasing the medication includes controlling the rate of releasing the medication to the eye by constructing the at least one pore with a specific geometry.

20. An ophthalmic insert for sustained release of medication to an eye, comprising:
    a body portion sized to pass through a lacrimal punctum and be positioned within a lacrimal canaliculus of an eyelid;
    a collarette connected to the body portion and sized to rest on the exterior of the lacrimal punctum, the collarette having at least one pore provided therein;
    an enlarged bulb portion connected to the body portion for securing the insert within the canaliculus;
    a reservoir contained at least partially within the body portion and in fluid communication with the at least one pore; and
    a medication stored within the reservoir in two phases including a concentrated form and a saturated solution, the medication released through the at least one pore and onto the eye over time in a controlled manner while the insert is positioned in the eyelid.

* * * * *